(12) United States Patent
Hong

(10) Patent No.: US 8,419,761 B2
(45) Date of Patent: Apr. 16, 2013

(54) BLOOD LANCET DEVICE

(75) Inventor: Kwan Ho Hong, Gwangmyoung-Si (KR)

(73) Assignee: GMMC, Seoul (KR)

( * ) Notice: Subject to any disclaimer, the term of this patent is extended or adjusted under 35 U.S.C. 154(b) by 356 days.

(21) Appl. No.: 12/530,318

(22) PCT Filed: Mar. 13, 2008

(86) PCT No.: PCT/KR2008/001429
§ 371 (c)(1),
(2), (4) Date: Sep. 8, 2009

(87) PCT Pub. No.: WO2008/111812
PCT Pub. Date: Sep. 18, 2008

(65) Prior Publication Data
US 2010/0087847 A1    Apr. 8, 2010

(30) Foreign Application Priority Data
Mar. 14, 2007    (KR) .................. 10-2007-0024927

(51) Int. Cl.
*A61B 5/151*    (2006.01)
(52) U.S. Cl.
USPC .......................................... 606/181; 606/172

(58) Field of Classification Search .......... 606/181–183, 606/167, 172; 600/583
See application file for complete search history.

(56) References Cited

U.S. PATENT DOCUMENTS

| | | | | |
|---|---|---|---|---|
| 2,823,677 A | * | 2/1958 | Hein, Jr. ........................ | 606/182 |
| 4,976,724 A | * | 12/1990 | Nieto et al. ................... | 606/181 |
| 5,318,583 A | * | 6/1994 | Rabenau et al. .............. | 606/182 |
| 5,423,847 A | * | 6/1995 | Strong et al. ................. | 606/182 |
| 5,730,753 A | * | 3/1998 | Morita ........................... | 606/181 |
| 6,210,420 B1 | * | 4/2001 | Mauze et al. ................. | 606/182 |
| 7,833,170 B2 | * | 11/2010 | Matsumoto et al. .......... | 600/583 |
| 2006/0100655 A1 | * | 5/2006 | Leong et al. .................. | 606/181 |

FOREIGN PATENT DOCUMENTS
WO    WO 2004054445 A1 *    7/2004

\* cited by examiner

*Primary Examiner* — Kathleen Sonnett
(74) *Attorney, Agent, or Firm* — Birch, Stewart, Kolasch & Birch, LLP

(57) ABSTRACT

This invention relates to a blood lancet device that is used to collect a small quantity of blood from a human body. More specifically, it relates to a blood lancet device that: can control the depth of the lancet needle's penetration of the skin; can push the lancet to eject; can accurately collect blood by ensuring linear motion; and can reduce the pain involved in blood collection.

8 Claims, 4 Drawing Sheets

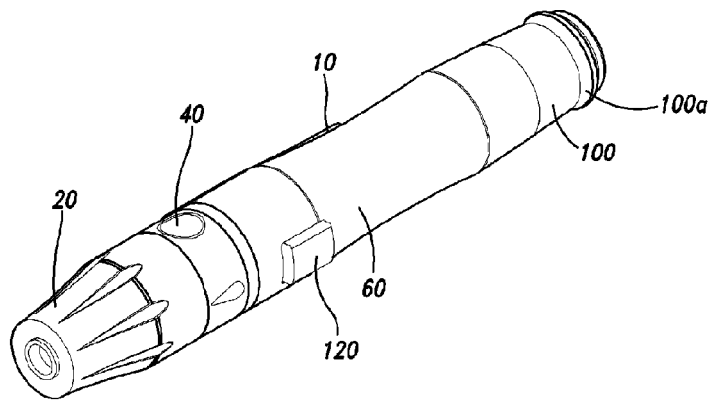
[Fig. 1]
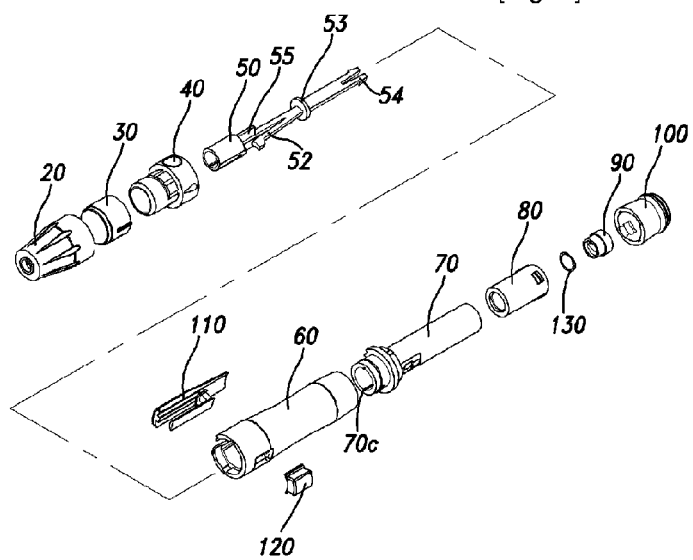
[Fig. 2]
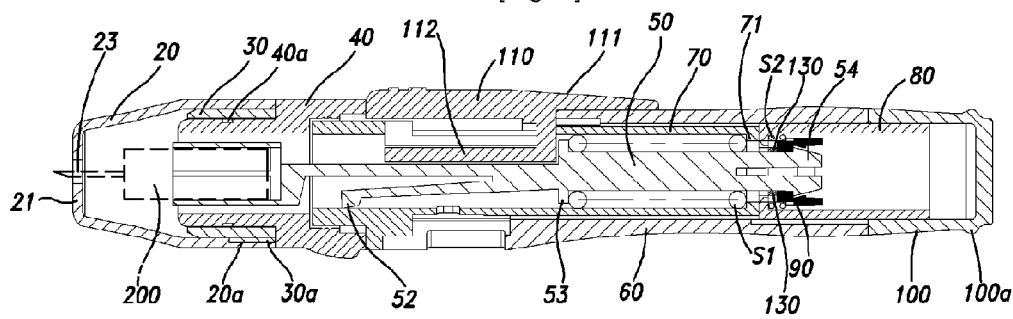
[Fig. 3]

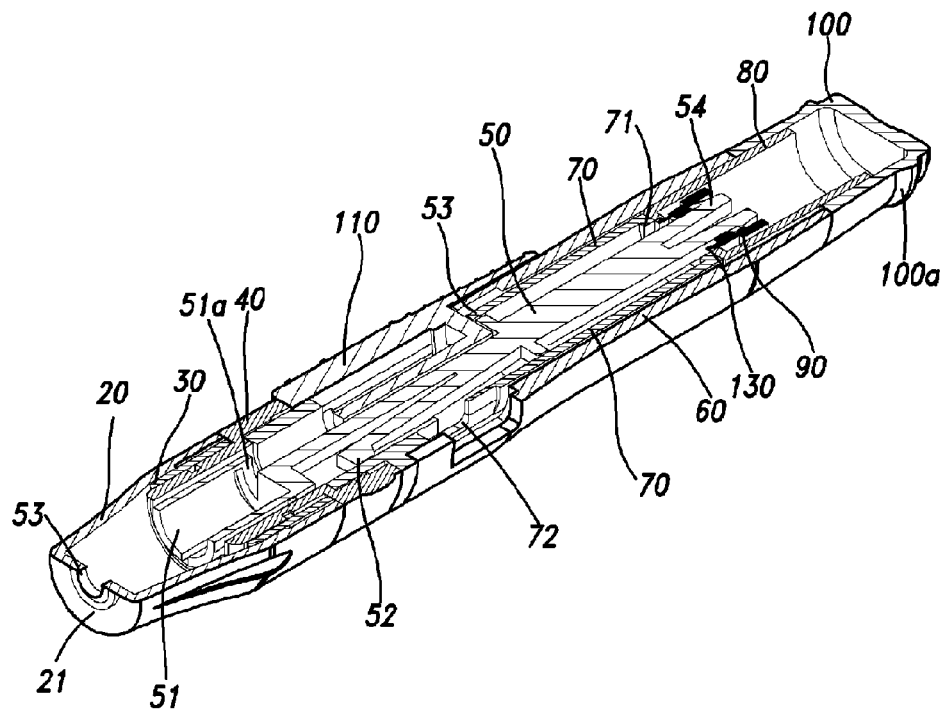
[Fig. 4]
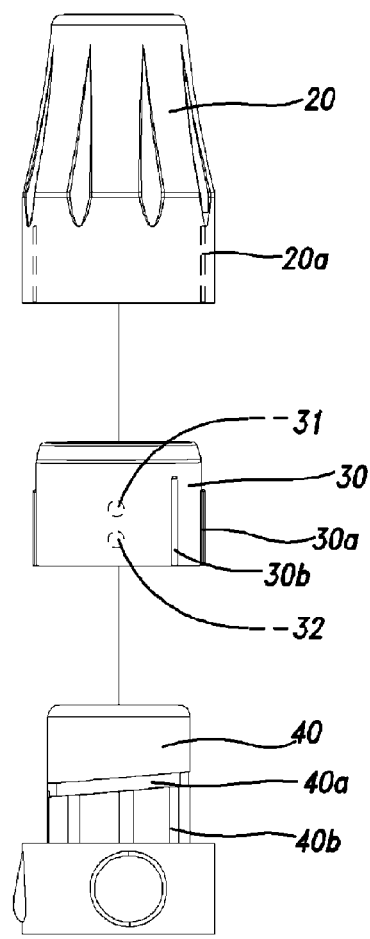
[Fig. 5]

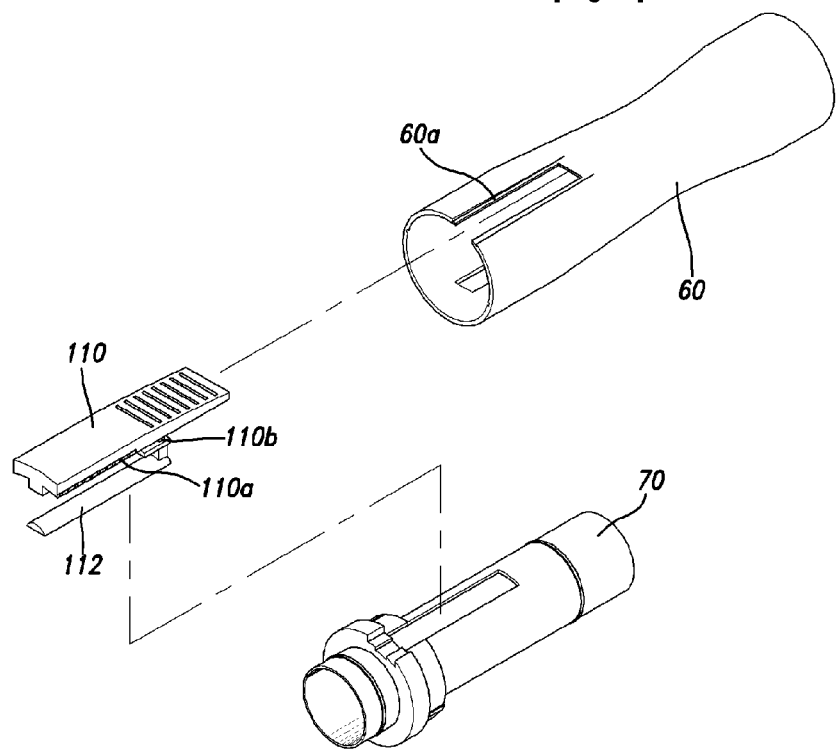
[Fig. 6]
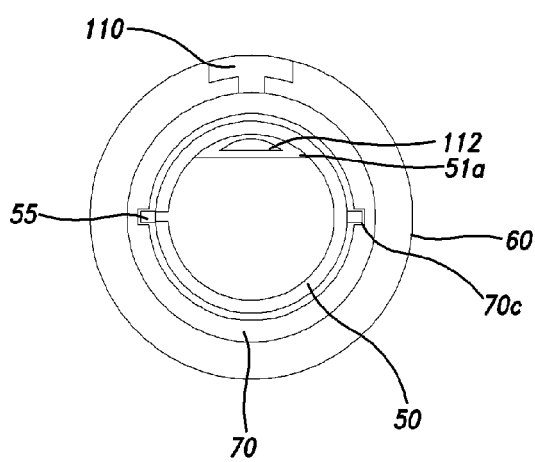
[Fig. 7]

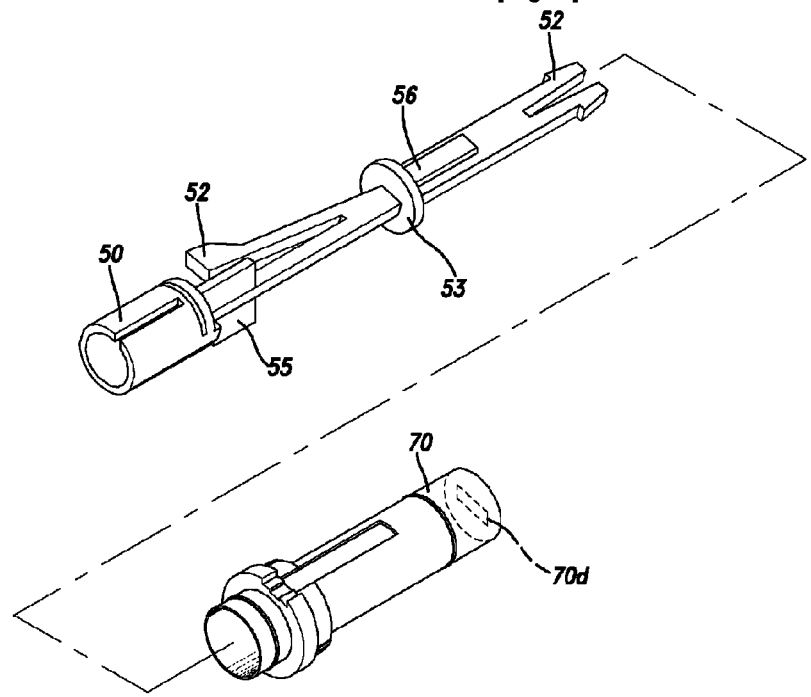
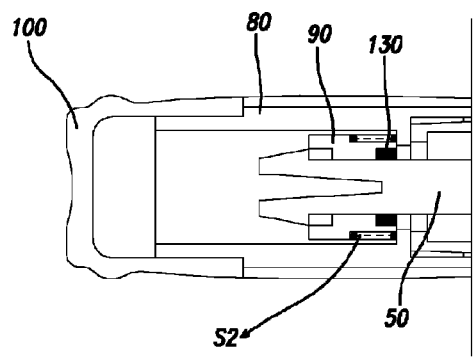
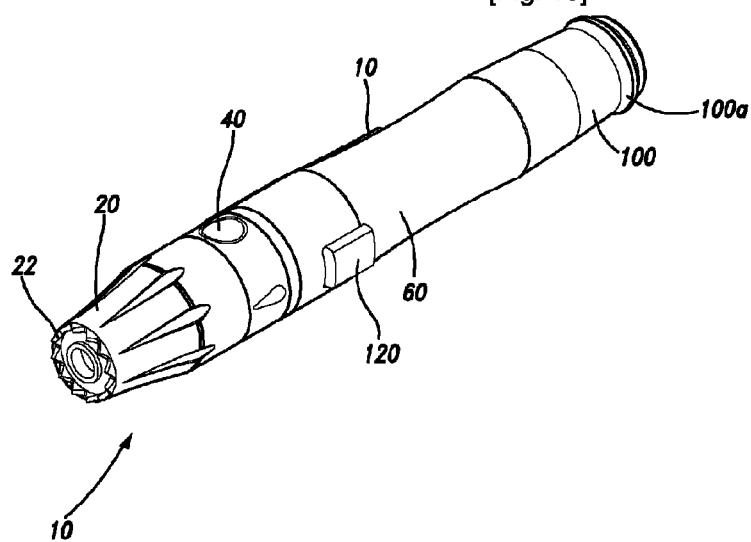

BLOOD LANCET DEVICE

TECHNICAL FIELD

This invention relates to a blood lancet device that is used to collect a small quantity of blood from the human body. More specifically, it relates to a blood lancet device that: can control the depth of the lancet needle that penetrates the skin; can push the lancet to force it to withdraw; can accurately collect blood by ensuring the linear motion of the needle; and can reduce the pain of blood collection.

BACKGROUND ART

Blood lancet devices are primarily used by diabetes patients who are required to regularly check their blood sugar levels, but they are also used in numerous other areas where the collection of blood is required. A blood lancet device is composed of a body and a lancet that is made of a needle fixed to the body. By giving elasticity to the lancet, the needle goes into the skin to a particular depth to collect blood. The U.S. Pat. No. 4,517,978 conforms to this description. In this patent, when a trigger is pressed after the lancet is inserted and the sleeve is pulled back, the lancet is fired forward. At this time, a needle briefly penetrates the skin and is then withdrawn.

In this type of blood lancet device, which was the type generally sold in the market, the depth of penetration achieved by the needle was uniformly fixed. However, people's skin can have different thicknesses, and blood needs to be collected from different parts of the body, so it was frequently necessary to adjust the depth of the needle's penetration of the skin. To achieve this, a device that could adjust the depth of penetration was developed. The U.S. Pat. No. 5,613,978 shows the structure of this device in detail. With the patented device, a user can adjust the depth of the needle's penetration of the skin by turning a control tip.

On the other hand, as a lancet penetrates the skin, in order to prevent infection it should be used only once. Therefore, the user should remove the lancet from the blood lancet device and dispose of it after use. Currently, users of the device, such as doctors or nurses, tend to pay less attention to the need to change the lancet as time goes on, so cases of infection often occur that are caused by the lancet needle.

As the lancet needle penetrates the skin, use of the lancet is accompanied by pain. People regard this pain as a natural aspect of blood collection.

DISCLOSURE OF INVENTION

Technical Problem

This invention was made to solve the problems with the existing technology. It purports to remove the lancet by pushing the ejector that is installed through the plunger into which the lancet is inserted, and at the same time, it intends to reduce pain from blood collection by ensuring the smooth linear motion of the needle and by preventing noise.

Technical Solution

The blood lancet device based on this invention has the features of: the plunger in whose front is inserted the lancet and in which the finger is formed; the outer tip that is assembled to cover the front of the plunger and that has a hole (through which the lancet needle goes) in the center of its front which is touched by the skin; and the ejector, a part of which is exposed to the outside of the outer sleeve that comprises the middle part of the blood lancet device, and the other part of which is used to eject the lancet of the plunger.

At the front of the outer tip, there is a sharp projection that causes pain when it contacts the skin.

Inside the outer tip, a ring is inserted and fixed, and then the inner tip is inserted and assembled. Inside the ring, there is a projection, which helps the ring to move forward and backward in the direction of the axis according to the outer tip's turning, engaged with the spiral groove formed on the ring, after being safely mounted on the spiral groove made on the inner tip. Here, on the surface of the inner tip, a location-determining groove is formed at every particular angle. Inside the ring, a projection is made, which is inserted into the location-determining groove.

The blood lancet device based on this invention has the features of: the plunger in whose front is inserted the lancet and in which the finger is formed; the outer tip that is assembled to cover the front of the plunger and that has a hole (through which the lancet needle goes) in the center of its front which is contacted by the skin; and the ejector, a part of which is exposed to the outside of the outer sleeve that comprises the middle part of the blood lancet device, and the other part of which is used to push the lancet of the plunger out. The plunger is inserted into a fixed tube. In the plunger, rails are made, which are inserted into rail grooves in the fixed tube. The rails guide the plunger to move forward and backward in a linear manner.

In the back of the fixed tube, a linear hole is made, through which the back of the plunger goes. In the plunger, a rise, which gets caught when the plunger is pulled back, is made.

At the end of the plunger, an end ring is inserted, but at the front of the end ring, a rubber ring is mounted for the prevention of noise.

In the ejector, a rail groove is made at both sides. The rails of the outer sleeve are inserted into the rail grooves.

In the ejector there are several projections, especially on the part that is touched by the fixed tube.

In addition, it is characteristic that the ejector is not sufficiently long to completely eject the lancet, even when it is compressed to the maximum.

Advantageous Effects

In the blood lancet device based on this invention, the lancet becomes separated by the ejector, reducing both the danger of infection and the pain resulting from the lancet's contact with the skin.

The blood lancet device based on this invention ensures the linearity of the plunger that transports the lancet, so scratching of the skin by the lancet is prevented. As a result, pain can be reduced.

The blood lancet device based on this invention has a rise at the back of the plunger, which means that in the event that a user pulls back the end cap excessively after pulling up the ejector with the left thumb for the removal of the lancet, any damage or malfunction of the ejector can be prevented.

The blood lancet device based on this invention uses rubber materials for the locations where parts contact each other, so noise is reduced.

BRIEF DESCRIPTION OF THE DRAWINGS

FIG. 1 is a perspective view of the blood lancet device based on this invention.

FIG. 2 is another perspective view of the disassembled blood lancet device based on this invention.

FIG. 3 is a cross-sectional view of the blood lancet device based on this invention.

FIG. 4 is another cross-sectional view of the blood lancet device based on this invention.

FIG. 5 shows the assembly of the outer tip and the inner tip, parts of the blood lancet device based on this invention.

FIG. 6 is a dissembled perspective view showing how the ejector, a part of the blood lancet device based on this invention, is assembled.

FIG. 7 is a front view of the ejector (illustrated in FIG. 6), assembled.

FIG. 8 is a perspective view of the plunger, which is a part of the blood lancet device based on this invention.

FIG. 9 is a partial cross-section, illustrating how the blood lancet device based on this invention moves forward when it is shot.

FIG. 10 shows another practical example of the blood lancet device based on this invention. It is a perspective view of the blood lancet device to which the pain-causing projections are applied.

BEST MODE FOR CARRYING OUT THE INVENTION

The blood lancet device based on this invention 10 is comprised of an outer tip 20, an inner tip 40, an outer sleeve 60, and an end cap 100, assembled in order from the front as illustrated in FIGS. 1~5. By turning the outer tip 20, it is possible to adjust the depth of the lancet 200 needle's penetration of the skin. Once the end cap 100 at the end is pulled back, the finger 52 of the plunger 50 gets caught in the trigger 120 and the spring S1 becomes contracted. Under this circumstance, if the trigger 120 is pressed, the plunger 50 momentarily moves forward, influenced by the elasticity of the spring S1, and the needle of the lancet 200 pricks the skin to penetrate it.

In the blood lancet device 10, the plunger 50 where the receptor 51, the front of which is inserted with the lancet 200, is formed, is installed. The plunger 50 moves forward and backward inside the fixed tube 70, and in the middle, there is a flange 53 to which the spring can be hooked. By the side, the finger 52, which is caught by the trigger 10, is made to go out elastically.

At the back of the plunger 50, there is a hook 54 on which the end ring 90 is hung. Therefore, if the end ring 90 moves backward, the plunger 50 moves, following the movement of the end ring. The fixed tube 70 has the plunger 50 within it so the flange is made in it, through which the inner tip 40 is screw-assembled at the front and the spring S1 is hung up in the back. The spring S1 is installed between the flange 53 of the plunger 50 and the flange of the fixed tube 70, so when the plunger 50 moves backward, the spring becomes contracted. Under this circumstance, if the trigger 120 is operated, the spring is momentarily released, creating elasticity and causing the plunger 50 to be pushed forward. At one side of the fixed tube 70, there is a cut 51a through which the ejector 110 passes and moves. At the other side, there is a hole 72 in which the finger 52 of the plunger 50 is inserted. In the hole 72, the trigger 120 is located.

The ejector 110 is composed of: the handle 111 that protrudes out; and the ejecting part 112 that moves in the direction of the axis and pushes the lancet 200. As illustrated in FIGS. 3 and 4, if the inner tip 40 which is combined with the fixed tube 70 through screws is disassembled, the handle 111 of the ejector 110 is then pushed forward, the ejecting part 112 moves forward and goes through the groove 51a of the receptor 51 of the plunger 50, pushing the lancet 200 gets out and detaching it.

The blood lancet device 10 based on this invention allows the adjustment of the depth of the lancet 200 needle's penetration of the skin through the following structure. As described above, at the front of the fixed tube 70, the inner tip 40 is combined with screws. As illustrated in FIG. 5, the inner tip is assembled with the fixed tube 70 at about the halfway point (from the back) of its total length, and the remaining front half has a layer, which reduces the outer diameter. At the front of the inner tip 40, spiral grooves 40a are made throughout 180 degrees. In addition, along the outer diameter, in the direction of the axis, a total of 8 location-determining grooves 40b are made, at every 45 degrees. The projections 31, 32, which are made on each ring 30, are inserted and assembled in the spiral grooves 40a and the location-determining grooves 40b. For the ring 30, along the direction of the axis, two linear rails 30a are made at the outer diameter, and two projections 31, 32 are made at the inner diameter. The rails 30a are inserted into the rail grooves 20a that are made at the inner diameter of the outer tip 2, so the outer tip 20 and the ring 30 turn together. One 31 of the two projections 31, 32 that are made at the inner diameter is inserted into the spiral groove 40a, and the other 32 is inserted into the location-determining groove 40b to determine a location. The ring 30 is forcibly inserted into the outer tip 20, so on the ring 30 two cuts 30b are made at 180 degrees, to enable easy turning. Therefore, if the outer tip 20 is turned under the circumstance in which it is assembled, the outer tip 20 turns, together with the ring 30 and the projections 31, 32 of the ring 30 turn along the spiral groove 40a of the outer tip 20, and move forward or backward. Through this process, the distance between the front end of the outer tip 20 and the lancet 200 is adjusted, consequently adjusting the depth of the needle's penetration of the skin.

FIG. 10 shows that at the front end of the outer tip 20, sawtooth-shaped pain-causing projections 22 surround the hole 23 of the outer tip 20. These sawtooth-shaped pain-causing projections 22 press the skin first when blood collection is attempted, stimulating the nerves in the pressed part so that at the moment the lancet 200 needle actually hits the skin, the pain is reduced.

On the surface of the fixed tube 70, the outer sleeve 60 is assembled. The outer sleeve 60 is open in the front and back. In order to receive the ejector 110 and the trigger 120, cuts are made on its sides. Inside the outer sleeve 60 at the back end of the fixed tube 70, a moving tube 80 with a diameter that is similar to the fixed tube 70 is inserted. Inside the moving tube 80, the end ring 90 upon which the hook 54 of the plunger 50 is hung, is inserted and assembled. The end ring 90 has a layer, so a short spring S2 is installed in the gap at the front end of the moving tube 80. This spring S2 absorbs shocks after the lancet 200 hits, pushing back the lancet slightly 200. At the back end of the moving tube 80, the end cap 100 is assembled, so the end cap 100 and the moving tube 80 move forward and backward together. At the end cap 100 there is a rise 100a, which improves convenience for the user.

The following is a description of how the blood lancet device based on this invention works.

A user can adjust the depth of the lancet 200 needle's penetration of his/her skin by turning the outer tip 20. With the outer tip 20's turning, the projection 31 of the ring 30 moves along the spiral grooves 40a. Through this process, the distance between the front end of the outer tip 20 and the lancet 200 is adjusted. After adjusting, the user can separate the inner tip 40 from the fixed tube 70, insert the lancet 200 into the receptor 51a of the plunger, and assemble the inner tip 40 again.

After assembling the inner tip 40, the user pulls the end cap 100 back, and the moving tube 80, the end ring 90, and the plunger 50 compress the spring S1 and move backward. While moving, the finger 52 gets caught in the trigger 120, and the lancet 200 is completely mounted. At this time, the user presses the front of the outer tip 20 to the skin, and then presses the trigger 120. At this time, because of the elasticity of the spring S1, the plunger 50 moves forward and the lancet 200 needle hits the skin. Simultaneously to this, the skin is pressed by the pain-causing projections, which reduces the pain of the actual penetration of the needle. Following this, the user separates the inner tip 40 again and pushes the ejector 110, completely separating the lancet 200. The user can then insert a new lancet 200 and assemble the inner tip 40. The pain-causing projections 22 can also be made to be replaceable.

FIGS. 7 and 8 show that the plunger 50 is inserted into the fixed tube 70, the rails 55 are formed on the plunger 50, and are inserted into the rail grooves 70c in the fixed tube 70 to guide the plunger to move forward and backward in a linear manner. Therefore, the plunger 50 that is shot by the strength of the spring S1 moves in an accurately straight line, which prevents the lancet 200 from scratching the skin. In addition, at the back of the fixed tube 70, a linear hole 70d, where the back of the plunger 50 passes, is formed. On the plunger 50, there is a rise 56 that is caught when the plunger is pushed back by a particular distance. When the left thumb pushes the ejector 110 up and excessively pulls back the end cap 100 in order to remove the lancet 200, the presence of the rise 56 prevents damage or malfunction of the ejector 110.

FIG. 9 shows that the end ring 90 is inserted into the end of the plunger 50, but the rubber ring 130 for the prevention of noise is mounted at the front of the end ring 90. Therefore, the rubber ring 130 can absorb the noise that is made when the end ring 130 hits, so quiet blood collection is possible. Of course, it is possible to use other shapes of rubber material rather than the rubber ring 130.

FIGS. 6 and 7 show that the rail grooves 110b are formed at both sides of the ejector 110, and in the rail grooves 110b, the rails 60a of the outer sleeve 60 are inserted, which prevents the back of the ejector 110 from being seriously impacted and broken. The ejector 110 has a large number of projections 110a on the part that is touched by the fixed tube 70. These projections make the user feel certain that the ejector 110 moves when it is pushed.

On the other hand, the ejector 110 pushes out the lancet after the lancet has been used. This invention has adjusted the length of the ejector 110 to prevent the lancet from being completely discharged when the ejector 110 is pushed, in the event that it is not ready for a shot. Therefore, a user should forcibly repeat the same action to completely eject the lancet. That is, in the event that the ejector 110 is completely pushed, a user should pull the end cap 100 back to completely remove the lancet from the plunger 50. As two operations are required, the user cannot help but pay more attention, and accordingly, accidental pushing of the ejector 110 or the lancet falling out is prevented.

INDUSTRIAL APPLICABILITY

The blood lancet device based on this invention can be used as a medical apparatus for diabetic patients who need to collect blood periodically.

The invention claimed is:

1. A blood lancet device, comprising:
   a housing;
   an inner tip at a first end of the housing, the inner tip having linear location grooves and a spiral groove on an exterior surface;
   a ring fitting over the inner tip, the ring having an outer surface that is continuous about an entire circumference of the ring along an entire length in an axial direction;
   a first projection and a second projection on an inner surface of the ring, the second projection axially spaced from the first projection;
   an outer tip fitting over the ring;
   rails on the outer surface of the ring, the rails extending in the axial direction;
   grooves on an inner surface of the outer tip, the rails fitting in the grooves on the inner surface of the outer tip; and
   a needle within the housing,
   wherein the first projection fits within one of the location grooves and the second projection fits within the spiral groove.

2. The blood lancet device of claim 1, wherein the location grooves are spaced about the exterior surface of the inner tip every 45 degrees.

3. The blood lancet device of claim 1, wherein the housing comprises an outer sleeve and a fixed tube within the outer sleeve.

4. The blood lancet device of claim 1, further comprising:
   a lancet retaining the needle; and
   a plunger extending from the lancet.

5. The blood lancet device of claim 4, further comprising a spring between the plunger and the housing.

6. The blood lancet device of claim 4, further comprising an ejector engaging the plunger and accessible from outside the housing.

7. The blood lancet device of claim 1, further comprising serrated projections at an end of the outer tip.

8. The blood lancet device of claim 3, further comprising
   a lancet retaining the needle;
   a plunger extending from the lancet, the plunger having a hook at a rear end, a flange in a middle portion, and a finger extending from the flange in an axial direction,
   wherein the fixed tube has a rear wall provided with an opening, the hook of the plunger extending through the opening and engaging the rear wall of the fixed tube.

* * * * *